(12) United States Patent
Asai et al.

(10) Patent No.: US 6,513,363 B2
(45) Date of Patent: Feb. 4, 2003

(54) GAS SENSOR AND METHOD OF PRODUCING THE SAME

(75) Inventors: Masahiro Asai, Aichi (JP); Satoshi Ishikawa, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/196,225

(22) Filed: Jul. 17, 2002

(65) Prior Publication Data

US 2002/0178788 A1 Dec. 5, 2002

Related U.S. Application Data

(62) Division of application No. 09/745,864, filed on Dec. 26, 2000, now Pat. No. 6,446,489.

(30) Foreign Application Priority Data

Dec. 27, 1999 (JP) ............................................ 11-369194

(51) Int. Cl.⁷ ................................................. G01N 27/46
(52) U.S. Cl. ..................................................... 73/31.05
(58) Field of Search ............................ 73/31.05, 31.06; 204/424–429

(56) References Cited

U.S. PATENT DOCUMENTS

| | | | |
|---|---|---|---|
| 4,299,859 A | 11/1981 | Romine | |
| 4,309,897 A | 1/1982 | Springer et al. | |
| 4,578,174 A | 3/1986 | Kato et al. | |
| 5,859,361 A | 1/1999 | Fukaya et al. | |
| 6,222,372 B1 | 4/2001 | Fukaya et al. | |
| 6,360,581 B1 * | 3/2002 | Murase et al. | 73/31.05 |
| 6,415,647 B1 * | 7/2002 | Yamada et al. | 73/31.05 |

FOREIGN PATENT DOCUMENTS

| | | |
|---|---|---|
| JP | 09-184822 A | 7/1997 |
| JP | 10-054821 A | 2/1998 |
| JP | 11-271254 A | 10/1999 |
| JP | 11-295263 A | 10/1999 |
| JP | 2000-258384 A | 9/2000 |

\* cited by examiner

Primary Examiner—Hezron Williams
Assistant Examiner—Michael Cygan
(74) Attorney, Agent, or Firm—Sughrue Mion, PLLC

(57) ABSTRACT

A gas sensor includes a sensor element and a housing having an accommodation hole in which the sensor element is disposed. The housing has at an axial end thereof a cold crimped portion which cooperates with a shoulder portion of the accommodation hole to fixedly hold therebetween the sensor element. The cold crimped portion has an inward flange section, a hollow cylindrical section and a bent section between the inward flange section and the cylindrical section. The cold crimped portion is shaped so as to vary in thickness suddenly at or adjacent the bent section so that the cold crimped portion is assuredly bent at a predetermined position. A method of producing a gas sensor is also provided.

6 Claims, 5 Drawing Sheets

FIG.5
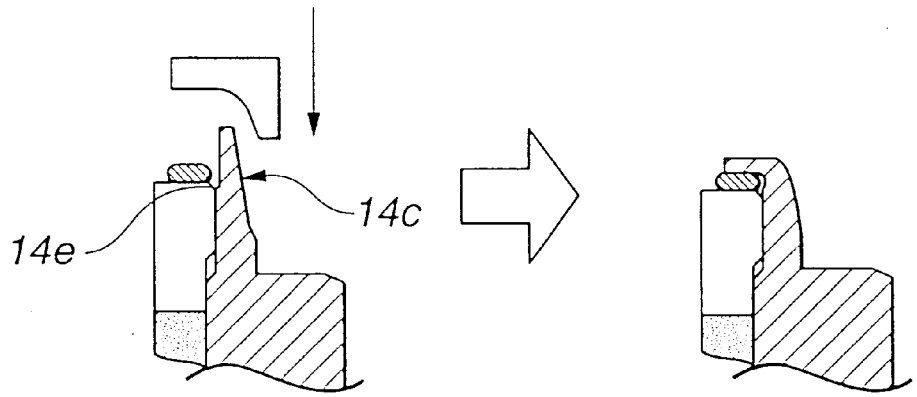
FIG.6A  FIG.6B
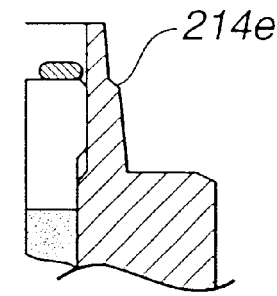 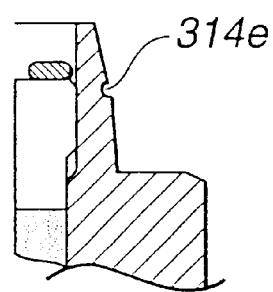
FIG.6C  FIG.6D
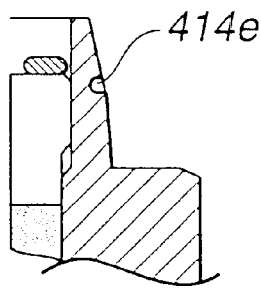 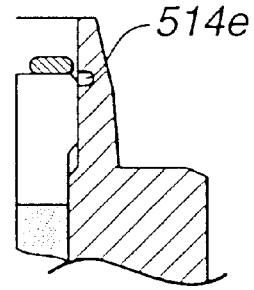

US 6,513,363 B2

GAS SENSOR AND METHOD OF PRODUCING THE SAME

This is a division of application Ser. No. 09/745,864 filed Dec. 26, 2000 now U.S. Pat. No. 6,446,484; the disclosure of which is incorporated herein by reference.

BACKGROUND OF THE INVENTION

The present invention relates to a gas sensor for detecting a concentration of a gas component in a gas such as an exhaust gas emitted from an internal combustion engine. The present invention further relates to a method of producing such a gas sensor.

An example of gas sensor is disclosed in U.S. Pat. No. 5,859,361. The sensor includes a sensor element which is fixedly held in a housing by crimping.

SUMMARY OF THE INVENTION

A problem of the prior art gas sensor is that crimping of the housing varies from product to product, i.e., the position at which a cold crimped portion of the housing is bent varies from product to product, thus causing the cold crimped portion to vary in size. Such a variation of the size of the cold crimped portion causes a variation of the compressive force applied to insulators disposed between the housing and the sensor element and therefore a variation of the stress caused in the insulators, thus causing a variation in the seal between the sensor element and the housing.

In case the housing is of the kind having a hot crimped portion additionally, such a variation of the size of the cold crimped portion causes a variation of the size of the hot crimped portion, thus causing the same problem as described above.

It is accordingly an object of the present invention to provide a gas sensor which can prevent a variation of the size of a cold crimped portion of a housing from product to product and therefore a variation of the compressive force applied to insulators disposed between the housing and a sensor element, and thereby can provide a reliable seal between the sensor element and the housing.

To accomplish the above object, there is provided according to an aspect of the present invention a gas sensor comprising a sensor element for detecting a concentration of a gas component in a gas, and a housing having an accommodation hole in which the sensor element is disposed, the housing having at an axial end thereof a cold crimped portion which cooperates with a shoulder portion of the accommodation hole to fixedly hold therebetween the sensor element, the cold crimped portion having an inward flange section, a hollow cylindrical section and a bent section between the inward flange section and the cylindrical section, the cold crimped portion being shaped so as to vary in thickness suddenly at or adjacent the bent section.

According to another aspect of the present invention, there is provided a gas sensor comprising a sensor element for detecting a concentration of a gas component in a gas, and a housing having an accommodation hole in which the sensor element is disposed, the housing having at an axial end thereof a cold crimped portion which cooperates with a shoulder portion of the accommodation hole to fixedly hold therebetween the sensor element, the cold crimped portion having an inward flange section, a hollow cylindrical section and a bent section between the inward flange section and the cylindrical section, the cold crimped portion having at or adjacent the bent section an annular soft section which is smaller in hardness than a remaining part thereof.

According to a further aspect of the present invention, there is provided a method of producing a gas sensor including a sensor element for detecting a concentration of a gas component in a gas, and a housing having an accommodation hole in which the sensor element is disposed, the housing having at an axial end thereof a cold crimped portion which cooperates with a shoulder portion of the accommodation hole to fixedly hold therebetween the sensor element, the cold crimped portion having an inward flange section, a hollow cylindrical section and a bent section between the inward flange section and the cylindrical section, the method comprising preparing the housing having the cold crimped portion which is hollow cylindrical before being crimped, providing the cold crimped portion, before being crimped, with a section where the cold crimped portion varies in thickness suddenly, and crimping the housing in such a manner that the cold crimped portion has the bent section at or adjacent the section where the cold crimped portion varies in thickness suddenly.

According to a further aspect of the present invention, there is provided a method of producing a gas sensor including a sensor element for detecting a concentration of a gas component in a gas, and a housing having an accommodation hole in which the sensor element is disposed, the housing having at an axial end thereof a cold crimped portion which cooperates with a shoulder portion of the accommodation hole to fixedly hold therebetween the sensor element, the cold crimped portion having an inward flange section, a hollow cylindrical section and a bent section between the inward flange section and the cylindrical section, the method comprising preparing the housing having the cold crimped portion which is hollow cylindrical before being crimped, providing the cold crimped portion, before being crimped, with an annular soft section which is smaller in hardness than a remaining part thereof, and crimping the housing in such a manner that the cold crimped portion has the bent section at or adjacent the annular soft section which is smaller in hardness than the remaining part thereof.

BRIEF DESCRIPTION OF THE DRAWINGS

FIG. 5 is a view similar to FIG. 3 but shows a crimping process according to a further embodiment;

FIGS. 6A to 6D are illustrations of various crimping processes according to modifications of the present invention;

DESCRIPTION OF THE PREFERRED EMBODIMENTS

Figure 1:
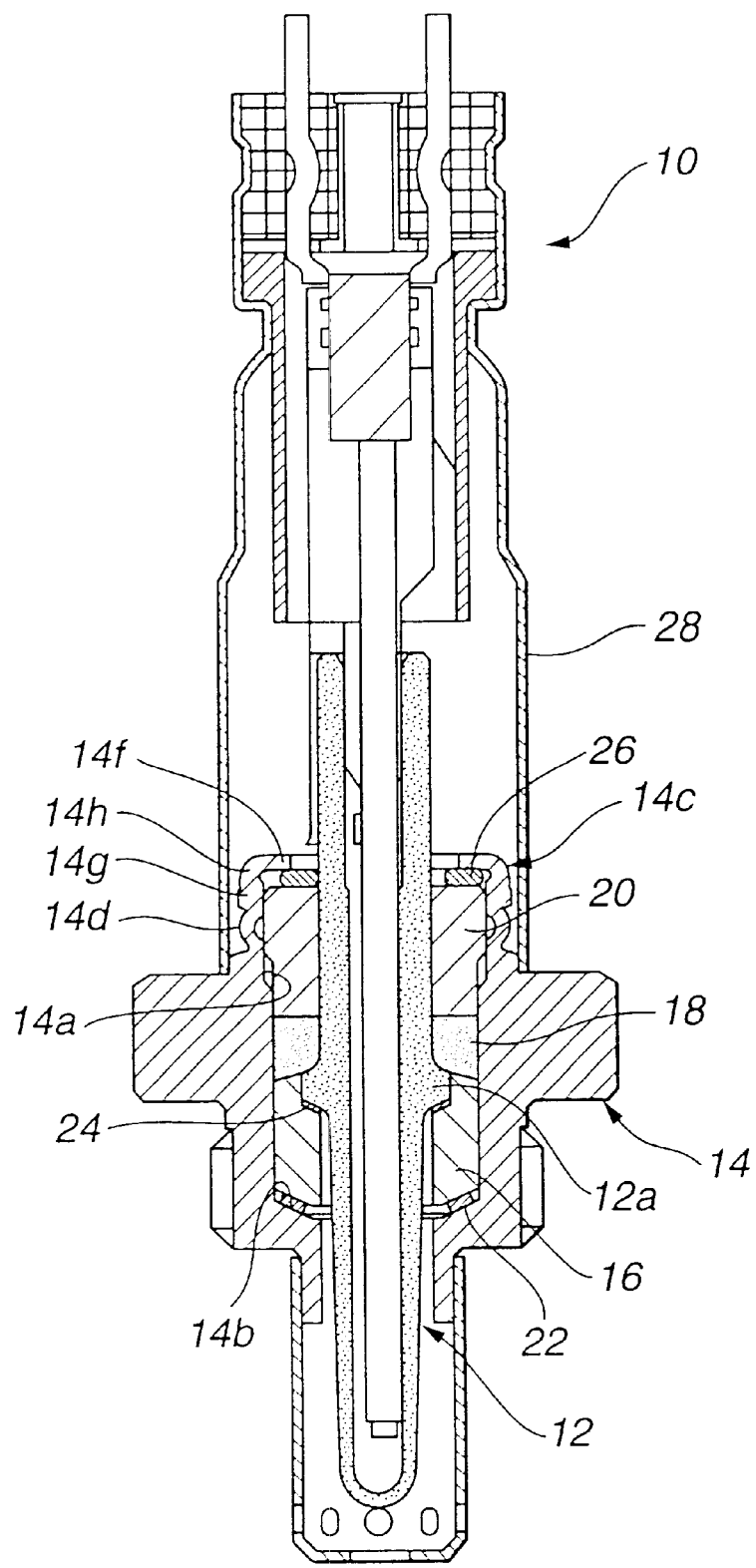
FIG. 1 is a sectional view of a gas sensor according to an embodiment of the present invention.

Referring first to FIG. 1, a gas sensor is generally indicated by 10. The gas sensor 10 is of the type for measuring the oxygen concentration in a measured gas and includes a sensor element 12 in the form of a tube closed at one end thereof. The sensor element 12 has a flange portion 12a serving as a stopper when inserted into a housing 14. The sensor element 12 is, for example, made of zirconia. Though not shown, the sensor element 12 is provided with a measuring electrode and a reference electrode on outer and inner surfaces thereof. A signal outputted from the electrodes is used to measure the oxygen concentration in the measured gas. This type of sensor is well known in the art and is not further described herein.

The housing 14 has an accommodation hole 14a in which the sensor element 12 is accommodated by interposing fillers or insulators 16, 18 and 20 between the housing 14 and the sensor element 12. The insulators 16 and 20 are made of alumina, and the insulator 18 is formed from insulating powder of talc. The accommodation hole 14a has a tapered shoulder portion 14b which cooperates with a cold crimped potion 14c to hold therebetween the sensor element 12 by way of the insulators 16, 18 and 20 while providing a hermetic seal between the sensor element 12 and the housing 14.

Figure 2A:
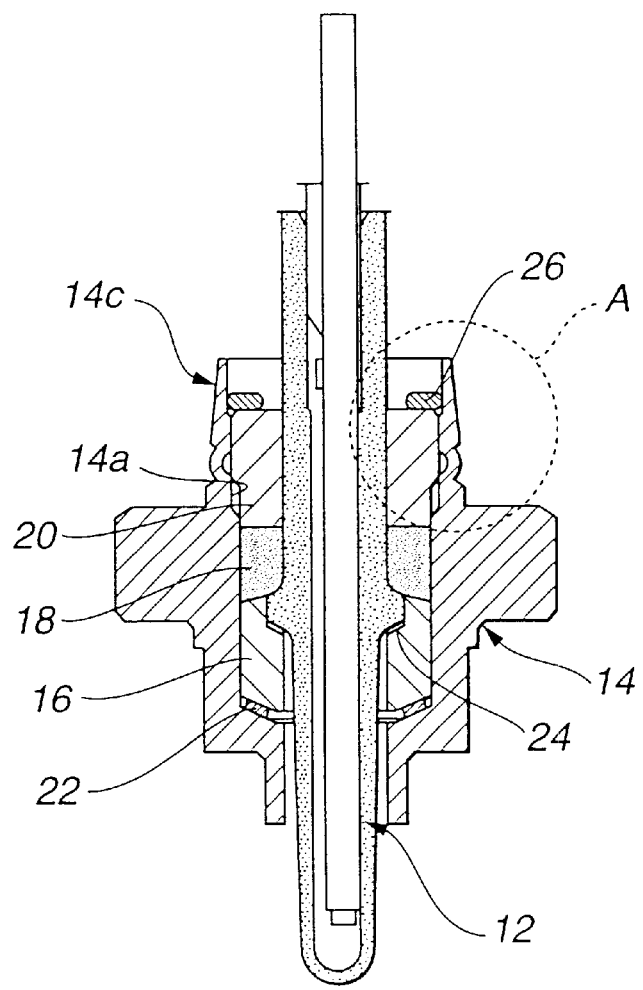
FIGS. 2A and 2B are illustrations of a crimping process of the gas sensor of FIG. 1.
Figure 2B:
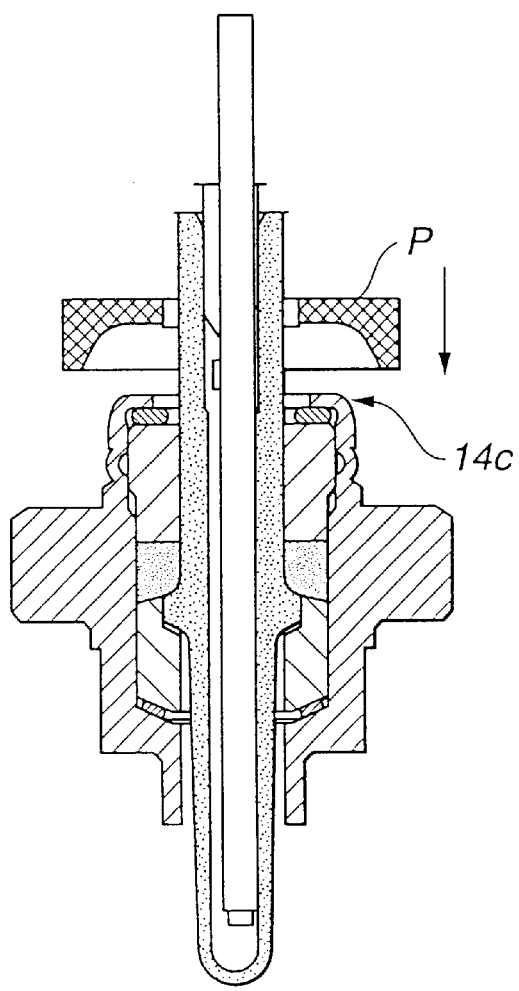

The cold crimped portion 14c is crimped by the processes shown in FIGS. 2A and 2B. Before crimping, the cold crimped portion 14c has such an upstanding, hollow cylindrical shape as shown in FIG. 2A. Upon crimping, the insulator 16 is inserted into the accommodation hole 14a of the housing 14 until it is brought into contact with the shoulder portion 14b of the housing 14 via a lower packing 22 made of stainless steel. Then, the sensor element 12 is inserted into the accommodation hole 14a of the housing 14 until it is brought into contact at the flange portion 12a (refer to FIG. 1) with the insulator 16 via a packing 24 made of stainless steel. Thereafter, insulating powder of talc constituting the insulator 18, the insulator 20 and a seal ring 26 made of stainless steel are placed on the flange portion 12a of the sensor element 12 in this order as shown. Subsequently, the cold crimped portion 14c of the housing 14 is crimped by means of a jig or die P under a crimping load of 25 KN for one second. Simultaneously with this crimping, a current is supplied from the die P to a hot crimped portion 14d of the housing 14 so that the hot crimped portion 14d is heated by the current flowing therethrough. By this, the hot crimped portion 14d in a state of being heated to a high temperature is caused to deform. When the hot crimped portion 14d is cooled to contract, the cold crimped portion 14c is caused to apply a compressive force to the insulating members 16, 18 and 20. The cold crimped portion 14c is thus crimped as shown in FIG. 2B while providing a hermetic seal between the housing 14 and the sensor element 12. Namely, the cold crimped portion 14c is shaped so as to include an inward flange section 14f, a hollow cylindrical section 14g and a bent section 14h between the inward flange section 14f and the cylindrical section 14g.

It is assumed that the above described variation of the size of the cold crimped portion is caused due to the fact that the cold crimped portion is constructed so as to have a bending strength which varies continuously around the bent section. Thus, after various trials and experiments, it was revealed by the inventors that accurate and uniform bending or crimping could be attained by providing the housing 14 with a section which is located at or adjacent the bent section 14h and at which the bending strength of the housing changes sharply or suddenly as compared with the section therearound and thereby allowing the deformation energy to concentrate at or adjacent the bent section 14h.

Figure 3:
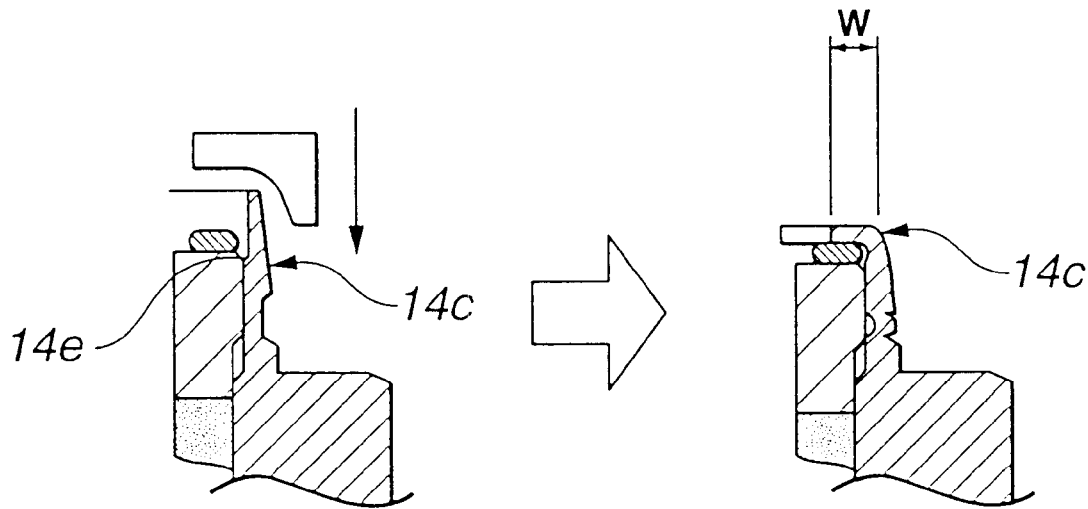
FIG. 3 is an enlarged view of a portion A of FIG. 2A, wherein the left-hand part is before being crimped and the right-hand part is after being crimped.

FIG. 3 shows an embodiment of the present invention. In this embodiment, the cold crimped portion 14c of the housing 14 has an inner peripheral wall which is formed with an annular shoulder 14e at or adjacent the bent section 14h. Such a shoulder can be formed by partly increasing the inner diameter of the cold crimped portion 14c, i.e., by making the inward flange section 14f thinner than the cylindrical section 14g. Such an increase of the inner diameter of the cold crimped portion 14c can be attained readily by drilling or by machining using a lathe. The cold crimped portion 14c is thus shaped so as to vary in thickness suddenly at or adjacent the bent section 14h. This embodiment makes it possible to attain an accurate crimping, i.e., makes it possible for the cold crimped portion 14c to be bent at a predetermined position assuredly or makes it possible for the products to be uniform in the size W, and therefore makes it possible to prevent the above noted variation of the size of the cold crimped portion 14c and therefore a variation of the compressive force applied to the insulators 16, 18 and 20.

Figure 7:
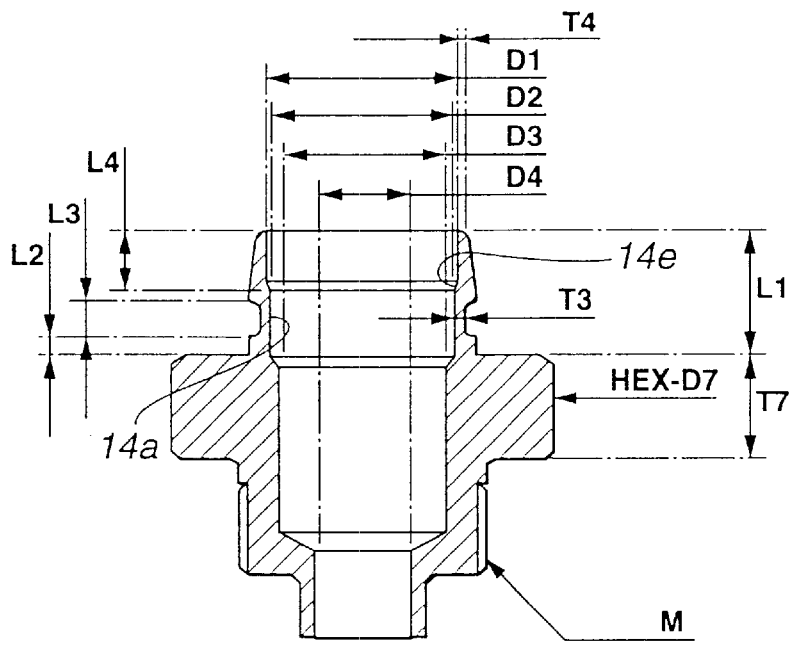
FIG. 7 is a sectional view of a housing of the gas sensor of FIG. 1.

More specifically, the housing 14 is structured as shown in FIG. 7. Namely, the accommodation hole 14a is so shaped as to have an upper end of a larger diameter D1 and stepwise reduce in diameter toward the lower end so as to have four smaller diameter portions of the diameters of D2 to D4. The portion of the accommodation hole 14a between the diameters D1 and D2 is formed as a tapered hole. The diameter D1 is 13.2 mm, D2 is 12.8 mm, D3 is 11.6 mm, and D4 is 7.5 mm. The housing 14 has a hexagonal portion of 22 mm in the width across flats D7 and 6.7 mm in the thickness T7. Under the hexagonal portion, the housing 14 is formed with an externally threaded portion of 18 mm in the nominal diameter M and 1.5 mm in pitch P. The length L1 of the hollow cylindrical portion extending from the upper end surface of the hexagonal portion to the upper end of the housing 14, is 11.0 mm. The hollow cylindrical portion has a lower end outer peripheral section which is perpendicular to the upper end surface of the hexagonal portion and which is 3 mm in height L2. To the lower end section of the tubular portion is welded by laser beam welding a cover 28 (refer to FIG. 1). Above the lower end outer peripheral section is provided a hot crimped portion which is 0.85 mm in the thickness T3 and 2.5 mm in the length L3. A cold crimped portion has an inner peripheral wall of 1.8 mm in the depth L4 and has a tip end section of 0.7 mm in the thickness T4.

Figure 8:
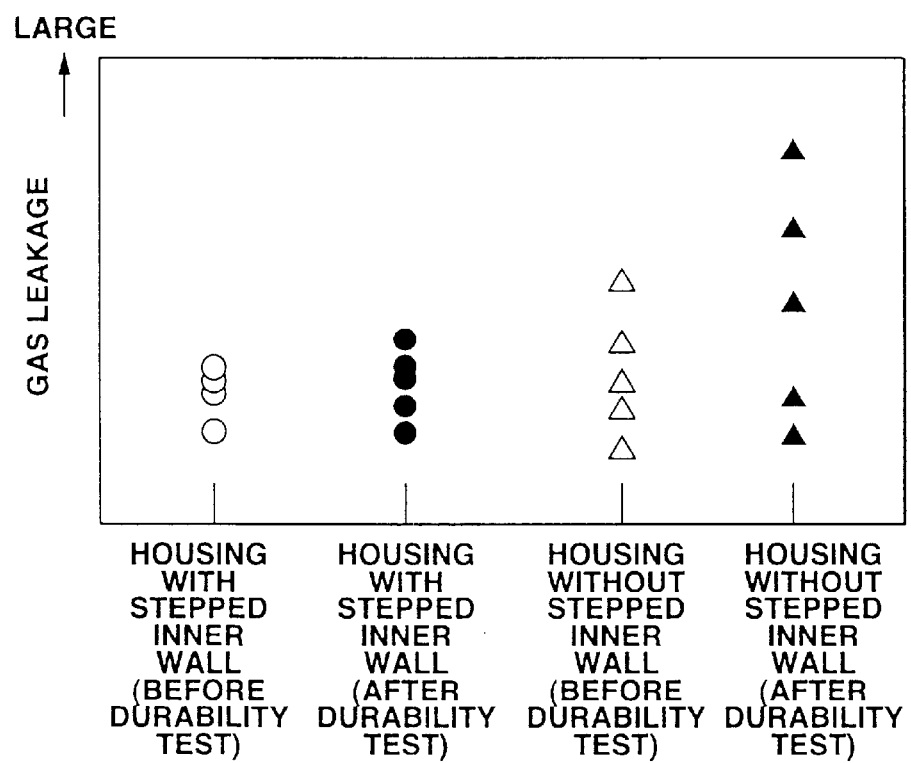
FIG. 8 is a graphic representation of the data concerning the sealing ability of the gas sensor of this invention by comparison with the comparative examples.

A comparative example of a gas sensor of the same structure except that the housing is not formed with the shoulder portion 14e, was prepared and compared with an example of the gas sensor 10 of this invention with respect to the hermetic seal between the housing and the sensor element. The examples of this invention and the comparative examples were tested for the sealing ability before and after being subjected to a durability test. In the durability test, the examples were mounted on an exhaust pipe of an automotive engine and operated for 1,000 hours under the condition in which the engine was operated at high speed and the temperature at the hexagonal portion of the housing was 750° C. The result is shown in FIG. 8. As will be seen from this graph, the variation of the hermetic seal of the gas sensor of this invention was smaller than that that of the comparative example. Further, from the comparison between the example of this invention and the comparative example with respect to the hermetic seal, it was found that a large deterioration in the hermetic seal occurred in some comparative examples.

Figure 4:
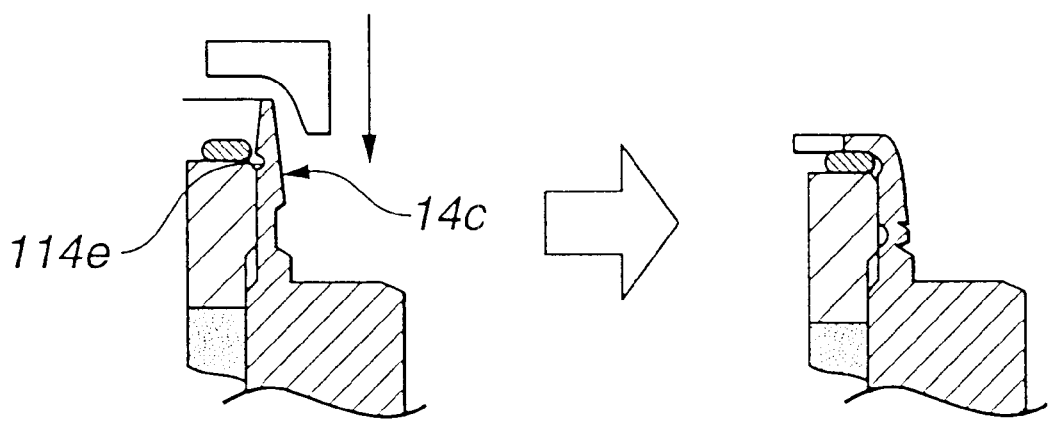
FIG. 4 is a view similar to FIG. 3 but shows a crimping process according to another embodiment.

FIG. 4 shows another embodiment. In this embodiment, the inner peripheral wall of the housing 14 is formed with an annular groove 114e at or adjacent a section to be formed into the bent section 14h, in place of the shoulder 14e. Except for the above, this embodiment is substantially similar to the previous embodiment of FIG. 3 and can produce substantially the same effect.

FIG. 5 shows a further embodiment. This embodiment is substantially similar to the previous embodiment of FIG. 3 except that the hot crimped portion 14d is not provided. This embodiment can produce substantially the same effect as the embodiment of FIG. 3.

FIGS. 6A to 6D show further embodiments.

In the embodiment of FIG. 6A, the cold crimped portion 14c of the housing 14 has at the outer peripheral wall a stepped or shoulder portion 214e.

In the embodiment of FIG. 6B, the cold crimped portion 14c has at the outer peripheral wall an annular groove 314e.

The embodiments of FIGS. 6A and 6B can produce substantially the same effect as the previous embodiment of FIG. 3.

In the embodiment of FIG. 6C, the cold crimped portion 14c has at the outer peripheral wall an annular soft section 414e which is softer, i.e., lower in hardness than a remaining part thereof. Such a soft section 414e can be formed by irradiating a laser beam onto the outer peripheral wall of the cold crimped portion 14c for thereby temporarily heating the bent section 14h up to a high temperature and thereafter allowing the bent section 14h to be annealed. This embodiment can produce substantially the same effect as the embodiment of FIG. 3 without requiring the housing 14 to be changed in shape by machining and therefore without changing the mechanical strength of the cold crimped portion 14c.

In the embodiment of FIG. 6D, the cold crimped portion 14c has at the inner peripheral wall an annular soft section 514e which is softer than a remaining part thereof.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

What is claimed is:

1. A gas sensor comprising:
   a sensor element for detecting a concentration of a gas component in a gas; and
   a housing having an accommodation hole in which the sensor element is disposed;
   the housing having at an axial end thereof a cold crimped portion which cooperates with a shoulder portion of the accommodation hole to fixedly hold therebetween the sensor element;
   the cold crimped portion having an inward flange section, a hollow cylindrical section and a bent section between the inward flange section and the cylindrical section;
   the cold crimped portion having at or adjacent the bent section an annular soft section which is smaller in hardness than a remaining part thereof.

2. A gas sensor according to claim 1, wherein the soft section is provided to an outer peripheral wall of the cold crimped portion and formed by irradiation of laser beam and annealing.

3. A gas sensor according to claim 1, wherein the soft section is provided to an inner peripheral wall of the cold crimped portion and formed by irradiation of laser beam and annealing.

4. A method of producing a gas sensor including a sensor element for detecting a concentration of a gas component in a gas, and a housing having an accommodation hole in which the sensor element is disposed, the housing having at an axial end thereof a cold crimped portion which cooperates with a shoulder portion of the accommodation hole to fixedly hold therebetween the sensor element, the cold crimped portion having an inward flange section, a hollow cylindrical section and a bent section between the inward flange section and the cylindrical section, the method comprising:
   preparing the housing having the cold crimped portion which is hollow cylindrical before being crimped;
   providing the cold crimped portion, before being crimped, with an annular soft section which is smaller in hardness than a remaining part thereof; and
   crimping the housing in such a manner that the cold crimped portion has the bent section at or adjacent the annular soft section which is smaller in hardness than the remaining part thereof.

5. A method according to claim 4, wherein the soft section is provided to an outer peripheral wall of the cold crimped portion before the crimping of the housing and formed by irradiation of laser beam and annealing.

6. A method according to claim 4, wherein the soft section is provided to an inner peripheral wall of the cold crimped portion before the crimping of the housing and formed by irradiation of laser beam and annealing.

* * * * *